(12) United States Patent
Daum et al.

(10) Patent No.: US 7,551,962 B2
(45) Date of Patent: Jun. 23, 2009

(54) IMPLANTABLE MEDICAL DEVICE WITH VOICE RESPONDING AND RECORDING CAPACITY

(75) Inventors: Douglas R. Daum, Lauderdale, MN (US); Qingsheng Zhu, Little Canada, MN (US); Bruce H. KenKnight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 288 days.

(21) Appl. No.: 11/071,984

(22) Filed: Mar. 4, 2005

(65) Prior Publication Data

US 2005/0240236 A1  Oct. 27, 2005

Related U.S. Application Data

(63) Continuation of application No. 10/215,237, filed on Aug. 8, 2002, now Pat. No. 6,865,424, which is a continuation of application No. 09/473,466, filed on Dec. 28, 1999, now Pat. No. 6,453,201, which is a continuation-in-part of application No. 09/421,746, filed on Oct. 20, 1999, now abandoned.

(51) Int. Cl.
*A61N 1/362* (2006.01)
(52) U.S. Cl. ............... 607/32; 607/2; 607/4; 607/5; 607/9; 607/17; 607/18; 607/27; 607/28; 607/30; 607/60; 600/508; 600/513; 600/528; 600/586

(58) Field of Classification Search ............... 607/1–2, 607/4–5, 9, 17, 18, 27–28, 30, 32, 59–60; 600/508, 513, 528, 586
See application file for complete search history.

(56) References Cited

U.S. PATENT DOCUMENTS

| | | | |
|---|---|---|---|
| 3,586,261 | A | 6/1971 | Palme |
| 3,623,486 | A | 11/1971 | Berkovits |
| 3,631,860 | A | 1/1972 | Lopin |
| 3,738,369 | A | 6/1973 | Adams et al. |
| 3,799,147 | A | 3/1974 | Adolph et al. |
| 4,066,086 | A | 1/1978 | Alferness et al. |

(Continued)

FOREIGN PATENT DOCUMENTS

WO       WO-97/43003        5/1996

OTHER PUBLICATIONS

"U.S. Appl. No. 09/473,466 Non-Final Office Action mailed Nov. 7, 2001", 8 pages.

(Continued)

*Primary Examiner*—Carl H Layno
*Assistant Examiner*—Deborah Malamud
(74) *Attorney, Agent, or Firm*—Schwegman, Lundberg & Woessner, P.A.

(57) ABSTRACT

An implantable medical device such as a cardiac pacemaker or implantable cardioverter/defibrillator with the capability of receiving communications in the form of speech spoken by the patient. An acoustic transducer is incorporated within the device which along with associated filtering circuitry enables the voice communication to be used to affect the operation of the device or recorded for later playback.

21 Claims, 1 Drawing Sheet

U.S. PATENT DOCUMENTS

| | | | |
|---|---|---|---|
| 4,628,939 | A | 12/1986 | Little et al. |
| 4,651,740 | A | 3/1987 | Schroeppel |
| 4,725,956 | A | 2/1988 | Jenkins |
| 5,012,815 | A | 5/1991 | Bennett, Jr. et al. |
| 5,040,212 | A | 8/1991 | Bethards |
| 5,205,285 | A | 4/1993 | Baker |
| 5,328,460 | A * | 7/1994 | Lord et al. .................... 604/67 |
| H1347 | H | 8/1994 | Greeninger et al. |
| 5,335,313 | A | 8/1994 | Douglas |
| 5,450,525 | A | 9/1995 | Russell et al. |
| 5,518,001 | A | 5/1996 | Snell |
| 5,529,578 | A | 6/1996 | Struble |
| 5,544,654 | A | 8/1996 | Murphy et al. |
| 5,544,661 | A | 8/1996 | Davis et al. |
| 5,594,638 | A | 1/1997 | Iliff |
| 5,615,380 | A | 3/1997 | Hyatt |
| 5,633,910 | A | 5/1997 | Cohen |
| 5,749,908 | A | 5/1998 | Snell |
| 5,752,976 | A | 5/1998 | Duffin et al. |
| 5,774,357 | A | 6/1998 | Hoffberg et al. |
| 5,792,204 | A | 8/1998 | Snell |
| 5,792,205 | A | 8/1998 | Alt et al. |
| 5,825,283 | A | 10/1998 | Camhi |
| 5,836,987 | A * | 11/1998 | Baumann et al. .............. 607/17 |
| 5,843,142 | A | 12/1998 | Sultan |
| 5,867,386 | A | 2/1999 | Hoffberg et al. |
| 5,875,108 | A | 2/1999 | Hoffberg et al. |
| 5,888,187 | A | 3/1999 | Jaeger et al. |
| 5,891,180 | A | 4/1999 | Greeninger et al. |
| 5,901,246 | A | 5/1999 | Hoffberg et al. |
| 5,903,454 | A | 5/1999 | Hoffberg et al. |
| 5,920,477 | A | 7/1999 | Hoffberg et al. |
| 5,921,938 | A * | 7/1999 | Aoyama et al. ............. 600/509 |
| 5,935,081 | A * | 8/1999 | Kadhiresan ................. 600/513 |
| 5,974,340 | A | 10/1999 | Kadhiresan |
| 5,987,352 | A * | 11/1999 | Klein et al. ................. 600/509 |
| 6,006,132 | A | 12/1999 | Tacker, Jr. et al. |
| 6,139,505 | A | 10/2000 | Murphy |
| 6,453,201 | B1 | 9/2002 | Daum et al. |
| 6,865,424 | B2 | 3/2005 | Daum et al. |
| 6,907,289 | B2 | 6/2005 | Stahmann et al. |
| 7,052,466 | B2 | 5/2006 | Scheiner et al. |
| 7,115,096 | B2 | 10/2006 | Siejko et al. |
| 7,123,962 | B2 | 10/2006 | Siejko et al. |
| 2005/0137490 | A1 | 6/2005 | Scheiner et al. |
| 2006/0282000 | A1 | 12/2006 | Zhang et al. |

OTHER PUBLICATIONS

"U.S. Appl. No. 09/473,466 Non-Final Office Action mailed Jun. 4, 2001", 9 Pages.
"U.S. Appl. No. 09/473,466 Notice of Allowance mailed Apr. 19, 2002", 5 pages.
"U.S. Appl. No. 09/473,466 Response file Sep. 4, 2001 to Non-Final Office Action mailed Jun. 4, 2001", 7 pages.
"U.S. Appl. No. 09/473,466 Response filed Feb. 7, 2002 to Non-Final Office Action mailed Nov. 7, 2001", 4 pages.
"U.S. Appl. No. 09/473,466 Supplemental Notice of Allowance mailed Jun. 26, 2002", 4 pages.
"U.S. Appl. No. 09/833,229 Advisory Action mailed Jul. 2, 2004", 3 pages.
"U.S. Appl. No. 09/833,229 Advisory Action mailed Sep. 14, 2005", 3 pages.
"U.S. Appl. No. 09/833,229 Final Office Action mailed Mar. 26, 2004", 12 pages.
"U.S. Appl. No. 09/833,229 Final Office Action mailed May 21, 2003", 14 pages.
"U.S. Appl. No. 09/833,229 Final Office Action mailed May 5, 2005", 7 pages.
"U.S. Appl. No. 09/833,229 Non-Final Office Action mailed Oct. 19, 2004", 10 pages.
"U.S. Appl. No. 09/833,229 Non-Final Office Action mailed Oct. 29, 2003", 13 pages.
"U.S. Appl. No. 09/833,229 Non-Final Office Action mailed Nov. 20, 2002", 11 pages.
"U.S. Appl. No. 09/833,229 Notice of Allowance mailed Nov. 10, 2005", 4 pages.
"U.S. Appl. No. 09/833,229 Response filed Jan. 18, 2005 to Non-Final Office Action mailed Oct. 19, 2004", 14 pages.
"U.S. Appl. No. 09/833,229 Response filed Jan. 29, 2004 to Non-Final Office Action mailed Oct. 29, 2003", 16 pages.
"U.S. Appl. No. 09/833,229 Response filed Oct. 6, 2003 to Final Office Action mailed May 21, 2003", 15 Pages.
"U.S. Appl. No. 09/833,229 Response filed Apr. 3, 2003 to Non-Final Office Action Mailed Nov. 20, 2002", 13 Pages.
"U.S. Appl. No. 09/833,229 Response filed May 25, 2004 to Final Office Action mailed Mar. 26, 2004", 14 pages.
"U.S. Appl. No. 09/833,229 Response filed Jun. 29, 2005 to Final Office Action mailed May 5, 2005", 12 pages.
"U.S. Appl. No. 09/833,229 Supplemental Response filed Jul. 23, 2004 to Advisory Action mailed Jul. 2, 2004", 14 pages.
"U.S. Appl. No. 09/833,229 Supplemental Response filed Sep. 29, 2005 to Advisory Action mailed Sep. 14, 2005", 10 Pages.
"U.S. Appl. No. 09/991,522 Non Final Office Action mailed Jul. 15, 2004", 17 pgs.
"U.S. Appl. No. 09/991,522 Notice of Allowance mailed Jan. 27, 2005", 5 pgs.
"U.S. Appl. No. 09/991,522 Response filed Oct. 15, 2004 to Non Final Office Action mailed Jul. 15, 2004", 9 pgs.
"U.S. Appl. No. 10/215,237 Final Office Action mailed Jul. 25, 2003", 7 pages.
"U.S. Appl. No. 10/215,237 Non-Final Office Action mailed Dec. 17, 2003", 4 Pages.
"U.S. Appl. No. 10/215,237 Non-Final Office Action Mailed Feb. 13, 2003", 10 Pages.
"U.S. Appl. No. 10/215,237 Notice of Allowability mailed Sep. 28, 2004", 3 Pages.
"U.S. Appl. No. 10/215,237 Notice of Allowance mailed Oct. 14, 2004", 4 Pages.
"U.S. Appl. No. 10/215,237 Response filed Nov. 25, 2003 to Final Office Action Mailed Jul. 25, 2003", 8 Pages.
"U.S. Appl. No. 10/215,237 Response filed Mar. 17, 2004 to Non-Final Office Action mailed Dec. 17, 2003", 6 Pages.
"Dream Hearing Aid Wish List", http://xp7.dejanews.com/getdoc.xp?recnu...db96q2&CONTEXT=862839689.31231&hitnum=0, Published by Deja News, Inc.,(1995),pp. 1-2.
"Future Medical Reports Strong First Quarter Results", http://www.growth.com/DMW/BISdmw.960517.html, Published by Berkshire Information Services, Inc.,(May 17, 1996),pp. 1-3.
"Future Medical Technologies International Announces Launch of New Products", http://www.growth.com/MENU/CVGR/PR/CVGR.950928.html, Published by Future Medical Technologies International,(May 5, 1997),1 page.
"Kurzweil AI and Link Announces Availability of Kurzweil Clinical Reporter for Invasive Cardiology with Datalink", http://www.kurzweil.com/press/971703_card.html, Published by Kurzweil Applied Intelligence, Inc.,(1996),pp. 1-4.
"Kurzweil Clinical Reporter", http://www.kurzweil.com/medical/kcr/faq.html, Published by Kurzweil Applied Intelligence, Inc. ,(1996),pp. 1-8.
"Voice Recognition Software in a Medical Office", http://www.voicerecognition.com/medical_office.html, Published by 21st Century Eloquence, Inc.,(May 5, 1997),pp. 1-5.
Silvermint, Emanuel H., et al., "Medical Device Programmer/Recorder/Monitor With Voice Recognition", U.S. Appl. No. 09/306,605, filed May 6, 1999, 42 Pages.

* cited by examiner

IMPLANTABLE MEDICAL DEVICE WITH VOICE RESPONDING AND RECORDING CAPACITY

CROSS-REFERENCE TO RELATED APPLICATIONS

This application is a continuation of U.S. patent application Ser. No. 10/215,237, filed on Aug. 8, 2002, issued on Mar. 8, 2005 as U.S. Pat. No. 6,865,424, which is a continuation of U.S. patent application Ser. No. 09/473,466, filed on Dec. 28, 1999, issued on Sep. 17, 2002 as U.S. Pat. No. 6,453,201, which is a continuation-in-part of U.S. patent application Ser. No. 09/421,746, filed on Oct. 20, 1999, now abandoned, which is incorporated herein by reference.

FIELD OF THE INVENTION

This invention pertains to implantable medical devices and to methods and systems for operating same. In particular, the invention relates to means for communicating with such devices.

BACKGROUND

Modern pacemakers typically have the capability to communicate data via a radio-frequency link with an external programming device. Such data is transmitted to the pacemaker in order to program its mode of operation as well as define other operating parameters. Data transmitted from the pacemaker can be used to verify the operating parameters as well as relay information regarding the condition of both the pacemaker and the patient. Pacemaker patients are monitored at regular intervals as part of routine patient care and to check the condition of the device. Among the data which may typically be telemetered from the pacemaker are its programming parameters and an electrogram representing the electrical activity of the heart as sensed by the pacemaker. Pacemakers have also been developed which monitor certain parameters over time while the device is functioning in the patient. Data representing these parameters can be stored in memory for later retrieval using an external programmer.

SUMMARY OF THE INVENTION

It would be desirable in certain situations to be able to communicate with an implantable medical device such as a pacemaker without the need for an external programming device or any kind of equipment such as a radio transmitter/receiver. This would enable a patient, for example, to alter the operation of the device by such communication at any time or place as the need arises. Furthermore, the data recording capabilities of the implantable medical device could be activated by the patient whenever subjective symptoms are noted. The recorded data could then be retrieved later and analyzed for correlation with the symptoms experienced by the patient.

Accordingly, in one embodiment, the present invention is an implantable medical device, such as a cardiac pacemaker or implantable cardioverter/defibrillator, having incorporated therein a system enabling voice communication with the device so that the device responds to voice commands. The system includes an acoustic transducer and processing circuitry for sensing a patient's voice and deriving messages from words spoken by the patient, which messages may then alter the operation of the device. When a patient in whom the device is implanted speaks, the vibrating chords of the larynx cause acoustical energy to be radiated into the thorax where the acoustic transducer converts the energy into electrical audio signals. The audio signals can be analyzed with speech recognition circuitry to recognize certain words that correspond to system messages which are then employed to affect the operation of the device. In certain embodiments of the device, the patient's spoken commands can be used to alter the operating mode of a pacemaker, change operating parameters, or initiate recording of physiological data for later retrieval. Such recorded data can include, for example, electrograms, recordings of the patient's voice, heart sounds, respiratory patterns, or indications of physical activity.

In another embodiment, the invention is an implantable medical device, such as a cardiac pacemaker or implantable cardioverter/defibrillator, having incorporated therein a system enabling voice recording by the device, with the voice recording activated by either an external or internal signal. In the case of externally activated voice recording, the external signal may be, e.g., a voice, tactile, or magnetic signal imparted to the device by the patient or physician. An internal signal may be generated by the device upon sensing a particular physiological condition via its sensing channels, where the particular condition would typically be defined as one where it would be useful to have the subjective impressions of the patient while the condition is present, such as during an arrhythmic episode.

DESCRIPTION OF THE INVENTION

Figure 1:
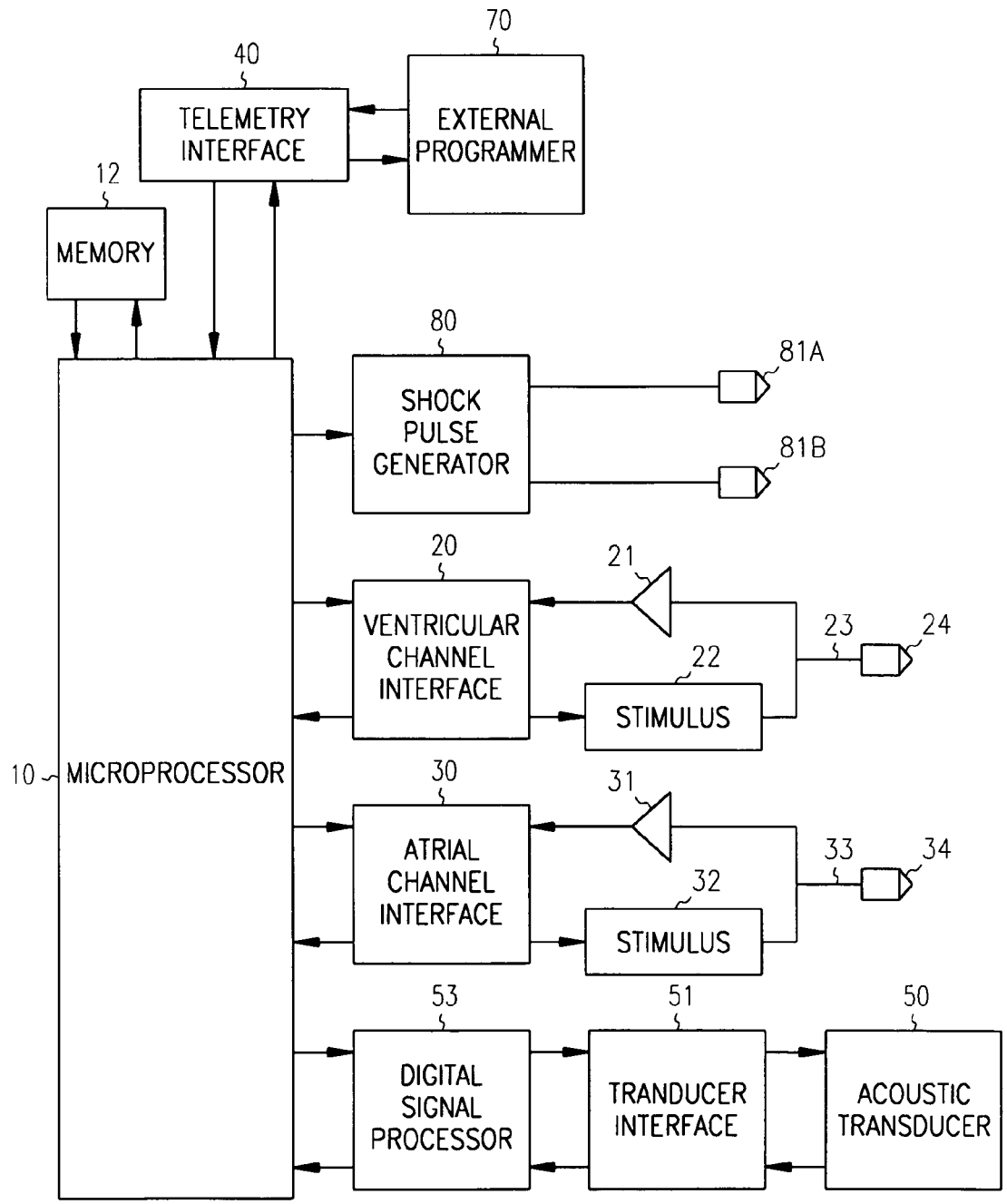
FIG. 1 is a system diagram of an implantable medical device incorporating the invention.

This application hereby incorporates by reference U.S. patent application Ser. No. 09/306,605, filed on May 6, 1999, now abandoned, in its entirety.

In the description that follows, a microprocessor-based pacemaker will be referred to as incorporating the present invention. It should be appreciated, however, the invention could also be incorporated into a pacemaker controlled by custom logic circuitry either in addition to or instead of a programmed microprocessor. The term "circuitry" as used herein should therefore be taken to mean either custom circuitry or a microprocessor executing programmed instructions contained in a processor-readable storage medium along with associated circuit elements.

FIG. 1 shows a system diagram of an implantable medical device, in this case is a microprocessor-based pacemaker with defibrillation and/or antitachycardia pacing capability, that incorporates the present invention. A microprocessor 10 communicates with a system memory 12 via a bidirectional system bus. Memory 12 may typically comprise a ROM for program storage and a RAM for data storage. The overall operation of the device is controlled by a system program running from the memory 12. The microprocessor also has a port for communicating with the telemetry interface 40 which in turn receives programming data from and transmits telemetry data to an external programmer 70 by a radio link. The pacemaker has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The channel interface includes sampling circuitry and an analog-to-digital converter for digitizing sensing signal outputs from the sensing amplifiers and registers which can be written to by the microprocessor in order to control pacing. A shock pulse generator 80 can also be interfaced to the microprocessor for delivering cardioversion or defibrillation pulses to the heart via a separate pair of electrodes 81*a* and 81*b*. Power for the device is provided by a battery.

An acoustic transducer 50 communicates with the microprocessor via a transducer interface 51. The transducer 50 may be an accelerometer or other piezo-resistive device capable of transducing acoustical energy from the patient's body into electrical signals. When the implantable medical device is implanted into a patient, the transducer 50 is capable of producing audio signals corresponding to the patient's voice, as acoustical energy produced by the patient's larynx is radiated into the thorax as well as into the air. The transducer interface 51 includes sampling circuitry for sampling the acoustic transducer output, an analog-to-digital converter for digitizing the samples, and circuitry for interfacing to a digital signal processor 53. Filtering of the transducer signals may also be performed by analog filters in the transducer interface 51 prior to digitization to reduce aliasing effects.

The digital signal processor interfaces to the microprocessor via the system bus and may incorporate speech recognition circuitry for extracting speech information from the digitized transducer signals. Such speech information may constitute specific groups of words that can be decoded into messages recognized by the system program. When such words are spoken by the patient, the messages cause the system program to alter the operation of the pacemaker. In different embodiments, a message derived from the speech information may cause the system program to alter the operation of the pacemaker by, for example, changing its operating mode, changing the operating parameters such as minimum heart rate, or causing the pacemaker to begin storage of sampled data in a storage medium such as the system memory 12.

Examples of such data storage include samples of the acoustic transducer output which therefore constitute recordings of the patient's voice or heart sounds, and samples of the sensing channel outputs thus forming a cardiac electrogram. Time stamps may also be applied to the recordings as they are made. Other types of data as recorded by other physiologic sensors incorporated into the device could also be recorded. The recordings can be later retrieved by transmission via the telemetry interface to an external programming device. Such recordings of physiological or voice data can then be correlated with symptoms experienced by the patient. This may be very useful to a treating physician in getting an accurate history of a cardiac event experienced by the patient, especially for those patients who are not able to adequately describe a cardiac event at much later clinical visit.

In another embodiment, voice recording is initiated upon receipt by the device of either an externally derived signal or an internal signal generated by the device itself. Examples of such external signals that could be used by particular embodiments are voice commands sensed and interpreted by the device as described above, operation of a magnetically-actuated reed switch with a magnet placed in proximity to the device (as is done to initiate a programming mode in conventional pacemakers), or manual operation of tactilely actuated switch by a user. In the case of a tactilely actuated switch, the tactile sensor actuating the switch could be, for example, a button placed on the outside of the implanted device which a user could access by pressing on the overlying skin, or a vibration sensor or accelerometer such as acoustic transducer 50 where acoustic signals generated by tactile stimuli applied to the device (e.g., by manually tapping) are interpreted as commands to activate voice recording. In another embodiment, voice recording could be activated when an internal signal is generated by the device when a condition corresponding to the onset of a physiologic or cardiac event is sensed by the device. In other embodiments, such externally and internally generated signals can be used to trigger other types of diagnostic storage including, e.g., recording of time stamps, cardiac electrograms, activity sensor outputs, and heart sound sensors, as well as to affect the operation of the device such as adjusting the pacing rate within predefined limits or turning on or off sensor dependent rate-responsive features.

In order to derive speech information from the acoustic transducer output corresponding to the patient's voice or to produce intelligible voice recordings for later playback, the acoustic transducer output must be sampled at some minimum rate. As both processor overhead and the memory requirements of the system increase with the sample rate, it is desirable to sample near this minimum rate. Although human hearing is capable of detecting audio frequencies up to 20 KHz, only a fraction of that bandwidth is needed to transmit normal speech. Phone lines in the U.S., for example, restrict the bandwidth of transmitted audio signals to below 4 KHz in order to prevent aliasing distortion when the signals are digitized. A level 0 digital signal used for transmitting a single voice channel over phone lines in the U.S., for example, is a pulse code modulated signal consisting of an analog voice signal sampled with 8 bits of quantization at a rate of 8000 samples per second. It has been found that intelligible speech can still result if an audio signal is bandlimited to at least as low as 2 KHz, which implies a minimum sampling rate of 4000 samples per second. At 4000 samples per second, a memory requirement of 80 Kilobytes would be needed for a 20 second recording. This FIGURE can be reduced still further using various data compression techniques.

The implantable medical device as described thus enables a patient to affect the operation of the device with voice commands. In order to prevent inadvertent commands being issued to the device and restrict access to its voice control feature, the system could be programmed to ignore all messages derived from transduced speech unless a specific password is first spoken. Another password could be used to cause further speech to be ignored. Alternatively, the voice control feature could be rendered inactive until a specific input signal is received which could be, for example, operation of a reed switch by a magnetic field similar to the way external programmers typically communicate with pacemakers, or operation of a tactile sensor incorporated into the device.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A system comprising:
an external device; and
an implantable medical device (IMD) comprising:
a pulse generator configured to provide at least one of pacing therapy pulses, cardioversion shock pulses, or defibrillation shock pulses to a heart;
an acoustic transducer configured to receive acoustic energy from within a patient's body and generating electrical audio signals in accordance therewith;

sampling circuitry and an analog-to-digital converter configured to produce digitized samples of a signal received from the acoustic transducer;

speech recognition circuitry configured to extract a voice command from the digitized samples;

circuitry configured to begin storing, in response to the voice command, a plurality of samples of the digitized acoustic signals including voice sounds in a storage medium; and a communication circuit operable to communicate with the external device, the communication circuit for communicating the recorded samples to the external device.

2. The system of claim 1, wherein the communication circuit includes a radio frequency (RF) link.

3. The system of claim 1, wherein the IMD further includes:

a sensing channel configured to sense electrical activity of the patient's heart in whom the device is implanted;

circuitry configured to produce digitized samples of the sensed electrical activity;

circuitry configured to record a plurality of samples of the digitized electrical activity signals in a storage medium in response to the voice command; and circuitry configured to apply a timestamp of when the acoustic signals were recorded, wherein the communication circuit is operable to communicate the recorded samples of electrical activity and time stamp to the external device.

4. The system of claim 3, wherein the external device is configured to correlate the recorded samples of the sensed electrical activity signal with patient symptoms.

5. The system of claim 1, wherein the digitized acoustic signals further include heart sounds.

6. The system of claim 1, wherein the digitized acoustic signals further include respiratory sounds.

7. The system of claim 6, wherein the communication circuit is configured to communicate stored samples of the respiratory sounds to the external device, and wherein the external device is configured to correlate the stored samples of the respiratory sounds with patient symptoms.

8. The system of claim 1, wherein the IMD further includes:

a sensor configured to sense patient activity, the sensor output providing electrical signals related to patient activity;

circuitry configured to record a plurality of samples of the patient activity signals in a storage medium in response to the voice command; and circuitry configured to apply a timestamp of when the acoustic signals were recorded, wherein the communication circuit is operable to communicate the recorded samples of patient activity and time stamp to the external device.

9. The system of claim 8, wherein the external device is configured to correlate the recorded samples of the patient physical activity signal with patient symptoms.

10. The system of claim 1, further including a filter circuit coupled to the acoustic transducer circuit, wherein the filter circuit is operable to band limit the electrical audio signals to two kilohertz (2 kHz) or less.

11. The system of claim 1, wherein the external device is configured to correlate the stored samples of the acoustic signal with patient symptoms.

12. The system of claim 1, wherein the circuitry to store the digitized samples is further configured to store the digitized samples using data compression.

13. The system of claim 1, wherein the IMD includes circuitry configured to generate an internal signal in response to detection of a physiologic event, and wherein the circuitry to store the digitized samples is activated upon generation of the internal signal.

14. The system of claim 13, wherein the internal signal is generated in response to detection of a cardiac arrhythmia.

15. The system of claim 1, wherein the IMD is configured to change a pacing rate in response to the voice command.

16. The system of claim 1, wherein the IMD is configured to change activation of a sensor dependent rate responsive feature of the IMD in response to the voice command.

17. The system of claim 1 wherein the IMD is configured to change an operating mode in response to the voice command.

18. The system of claim 17, wherein the IMD is configured to activate antitachycardia pacing in response to the voice command.

19. A system comprising:

an external device; and an implantable medical device (IMD) comprising:

an acoustic transducer configured to receive acoustic energy from within a patient's body and generating electrical audio signals in accordance therewith;

sampling circuitry and an analog-to-digital converter configured to produce digitized samples of a signal received from the acoustic transducer;

speech recognition circuitry configured to extract a voice command from the digitized samples;

a shock pulse generators wherein the IMD is configured to change an operating mode of the shock pulse generator in response to the voice command;

circuitry configured to begin storing, in response to the voice command, a plurality of samples of the digitized acoustic signals including voice sounds in a storage medium; and a communication circuit operable to communicate with the external device, the communication circuit for communicating the recorded samples to the external device.

20. The system of claim 19, wherein the IMD includes circuitry configured to generate an internal signal in response to detection of a physiologic event, and wherein the circuitry to store the digitized samples is activated upon generation of the internal signal.

21. The system of claim 20, wherein the internal signal is generated in response to detection of a cardiac arrhythmia.

* * * * *

UNITED STATES PATENT AND TRADEMARK OFFICE
CERTIFICATE OF CORRECTION

PATENT NO.         : 7,551,962 B2
APPLICATION NO. : 11/071984
DATED               : June 23, 2009
INVENTOR(S)      : Douglas R. Daum et al.

Page 1 of 1

It is certified that error appears in the above-identified patent and that said Letters Patent is hereby corrected as shown below:

In column 6, line 23, in Claim 17, delete "claim 1" and insert -- claim 1, --, therefor.

In column 6, line 39, in Claim 19, delete "generators" and insert -- generator, --, therefor.

Signed and Sealed this

Third Day of November, 2009

David J. Kappos
*Director of the United States Patent and Trademark Office*